United States Patent [19]
Mulier

[11] Patent Number: 5,314,451
[45] Date of Patent: May 24, 1994

[54] REPLACEABLE BATTERY FOR IMPLANTABLE MEDICAL DEVICE

[75] Inventor: Peter M. J. Mulier, St. Paul, Minn.

[73] Assignee: Medtronic, Inc., Minneapolis, Minn.

[21] Appl. No.: 6,099

[22] Filed: Jan. 15, 1993

[51] Int. Cl.$^5$ ............................................... A61N 1/02
[52] U.S. Cl. ........................................ 607/33; 607/36; 607/34
[58] Field of Search ............................ 607/33, 36, 34

[56] References Cited
U.S. PATENT DOCUMENTS

| | | |
|---|---|---|
| 3,942,535 | 3/1976 | Schulman . |
| 4,010,760 | 3/1977 | Kraska . |
| 4,119,103 | 10/1978 | Jirak . |
| 4,197,850 | 4/1980 | Schulman . |
| 4,232,679 | 11/1980 | Schulman . |
| 4,375,817 | 3/1983 | Engle . |
| 4,384,585 | 5/1983 | Zipes . |
| 4,445,511 | 5/1984 | Cowdery . |
| 4,469,104 | 9/1984 | PeerTrevarto . |
| 4,548,209 | 10/1985 | Wielders . |
| 4,693,253 | 9/1987 | Adams . |
| 4,830,006 | 5/1989 | Haluska . |
| 4,922,607 | 5/1990 | Doan . |

Primary Examiner—William E. Kamm
Assistant Examiner—Kennedy J. Schaetzle
Attorney, Agent, or Firm—Reed A. Duthler; Harold R. Patton

[57] ABSTRACT

An implantable electromedical device having a detachable, replaceable power supply. In one embodiment, the circuitry for an electromedical device is contained in a first hermetic enclosure, while a power supply for the device is contained in a second hermetic enclosure. The two enclosures are coupled together via a multiple conductor lead or the like, using any of the known assemblies commonly used for connection of pacing/sensing leads to an implantable device. A control signal generated by the device is applied to a control terminal on the battery enclosure. When the control signal is asserted, the battery is electrically coupled to two battery terminals on the battery enclosure, which terminals are coupled to power input terminals on the device itself. When the control signal is deserted, the battery is decouple from the battery terminals, so that there is no leakage current associated with the conduction of battery voltages on the connector between the two hermetic capsules. The disclosed arrangement may be advantageously utilized to allow for replacement of depleted batteries without explanation of the medical device itself, and to allow for different batteries to be used with the same device in different patients.

5 Claims, 3 Drawing Sheets

REPLACEABLE BATTERY FOR IMPLANTABLE MEDICAL DEVICE

BACKGROUND OF THE INVENTION

This invention relates to the field of medical devices, and more particularly relates to battery-powered implantable medical devices.

It has been proposed in the prior art that it would be desirable to provide an implantable medical device having a power supply that is separate from the remaining components, so that when the power supply becomes depleted, the battery can be replaced without replacing the device itself. A device with a detachable and replaceable battery would also offer the advantage that different sized batteries can be utilized in accordance with patients' individual needs. One arrangement for providing a removable battery in an implantable medical device was proposed in U.S. Pat. No. 4,010,760 to Kraska et al., entitled "Coupling Assembly for Implantable Electromedical Devices", which patent is hereby incorporated by reference in its entirety.

When an implantable device having its power supply and electronics in a single housing is produced, steps can be taken during manufacture to ensure that the amount of water vapor in the housing is very low, on the order of ten parts per million (PPM) or so. The hermetic seals provided by the welded seams in typical implantable device housings are extremely effective in preventing body fluid from entering the housing. Thus, current leakage within the device due to fluid leakage is not generally a problem.

However, hermetically sealed connectors for use external to such device housings are not available. Typical implantable connector systems employing sealing rings or other similar sealing mechanisms are not hermetically sealed. In the absence of a hermetic seal, fluid will inevitably enter the connector. Since the terminals connecting a replaceable battery to a medical device will be at different potentials, if any significant fluid ingress occurs, current leakage will occur across the fluid, resulting in a potentially significant drain on the power supply, and creating the potential for corrosion. The Kraska et al reference proposes a solution to the problem of corrosion due to the expected fluid ingress by appropriate selection of connector metals. However, the Kraska et al reference does not address the problem of the resulting leakage current.

Connector systems designed for use in connecting implantable leads to pulse generators, for example, typically display leakage resistances in the range of 50 k-ohms. These connector systems employ sealing rings (similar to the Kraska et al reference) to separate each connector surface and to seal entry to the connector assembly. If a connector assembly of the type designed for coupling a lead to an implantable device were used for the alternate purpose of conveying battery voltage to an implanted device a 50-kΩ leakage resistance of a lead connector assembly would allow leakage currents in the range of 60 microamps or more, depending on battery voltage. In the context of an implantable pacemaker, this current leakage may well exceed the current drain of the pacemaker by a factor of 10 or more, which would be clearly unacceptable.

SUMMARY OF THE INVENTION

In accordance with the present invention, a practical arrangement is provided whereby an implantable device, such as an implantable pacemaker, defibrillator, nerve stimulator or drug dispenser, or the like, may be powered by a separate, detachable power supply which can be removed and replaced independently from the implanted device itself.

A hermetically sealed external battery assembly having first and second battery terminals is coupled to a separate, hermetically sealed implantable device via conventional electrical connectors, as presently used to connect leads to implantable pacemakers. The problem of leakage current is addressed by the provision of a switch hermetically sealed within the battery housing. The switch is activated by means of a control signal from the implanted device and is similarly coupled to the device via a conventional electrical connector. During operation, the implantable device provides a logic signal to the switch to connect the external battery to the implanted device, as needed. The external battery may be employed to recharge an internal power source within the device, such as a capacitor or rechargeable battery, typically of much smaller capacity and size than the external battery.

Because the battery voltage is only provided to the device for as long as it takes to charge the device's internal electrical storage device, conventional lead connector technology or the like, which would normally be unsuitable for continuously coupling a battery to an implantable device, can be used. The current drain is presumed to be present while the battery is connected, but because it is only intermittently connected, the effect of the expected current drain is minimized.

In the embodiment illustrated, the invention takes the form of an implantable pacemaker/cardioverter/defibrillator. In this embodiment the external battery is employed to charge the high voltage output capacitors used to deliver defibrillation and cardioversion pulses. This voltage is applied to charging circuitry in the device until a desired level of charge has been established on the device's output capacitors. When the control signal ends, the external battery is decouple from the device, so that no voltage differential appears between any of the electrical connectors.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

The illustrated embodiment of the invention takes the form of an implantable pacemaker/cardioverter/defibrillator. In this embodiment, the invention is employed both to provide power charge the high voltage output capacitors and to recharge an internal battery within the device, which powers the low voltage circuitry. However, if the invention is practiced in the context of a cardiac pacemaker, implantable nerve stimulator or implantable drug dispenser, it is believed that the invention will be primarily employed to recharge an internal battery within the device.

Figure 1:
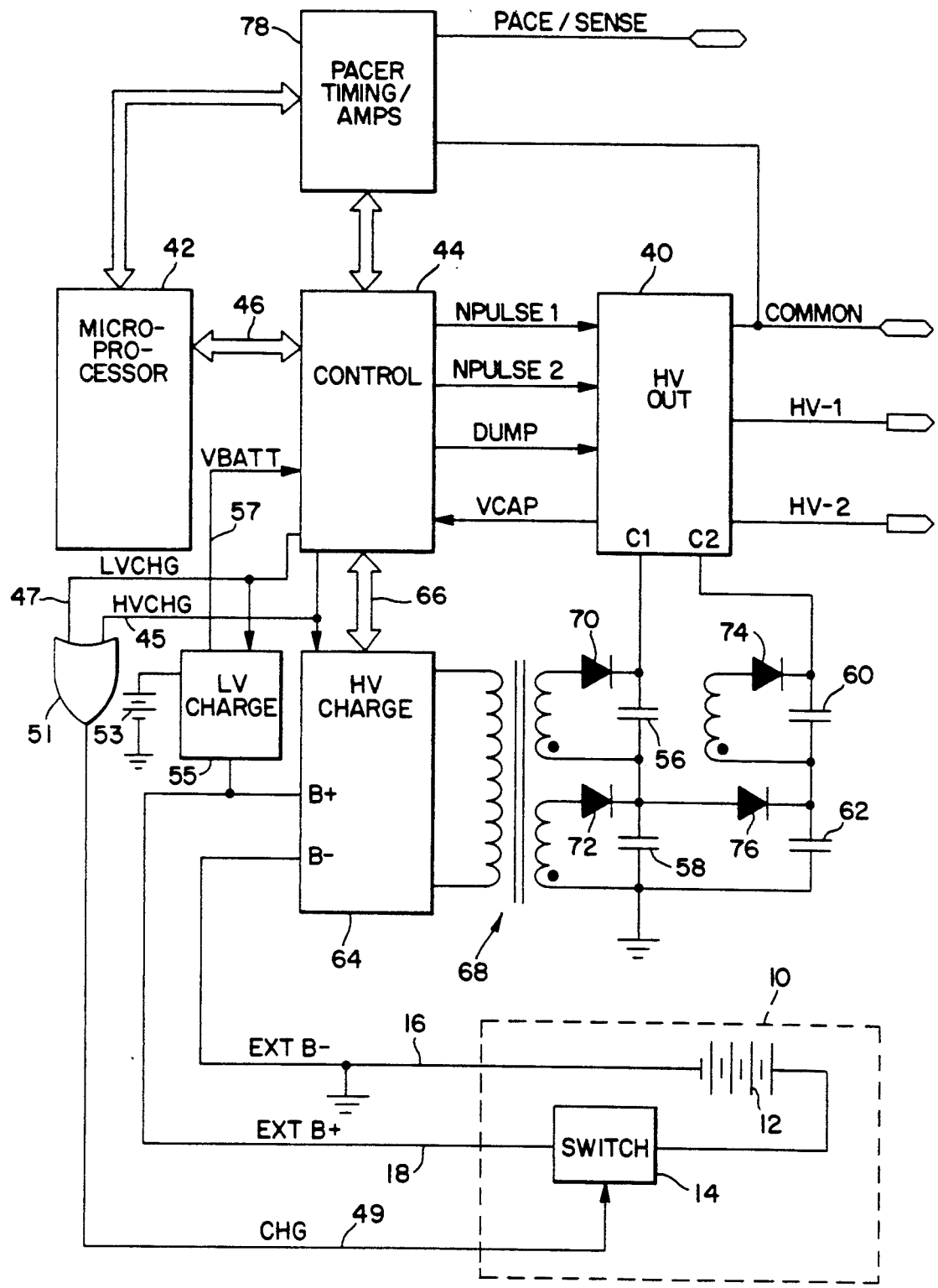
FIG. 1 is a block diagram illustrating a pacemaker/cardioverter/defibrillator having a detachable battery in accordance with one embodiment of the present invention.

Referring to FIG. 1, there is shown a block diagram illustrating the components of an implantable pacemaker/cardioverter/defibrillator in accordance with a presently preferred embodiment of the invention. Although the present invention will be described herein in the context of the device of FIG. 1, it is contemplated that the present invention can be advantageously incorporated into many various types of battery-powered implantable devices, such as cardiac pacemakers, nerve and muscle stimulators and implantable drug dispensers.

As illustrated in FIG. 1, the device is controlled by means of a stored program in a microprocessor 42, which performs all necessary computational functions within the device. Microprocessor 42 is linked to control circuitry 44 by means of a bidirectional data/control bus 46, and thereby controls operation of output circuitry 40 and high-voltage charging circuitry 64. On reprogramming of the device, for example by means of a telemetry system not shown in the figures, or upon occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals monitored and controlled by the timers in pace/sense circuitry 78. The basic operation of such a system in the context of an implantable pacemaker/cardioverter/defibrillator may correspond to any of the systems known in the art, and in particular may correspond generally to those illustrated in U.S. Pat. No. 4,548,209 to Wielders et al., U.S. Pat. No. 4,693,253 to Adams, U.S. Pat. No. 4,375,817 to Engle et al., U.S. Pat. No. 4,384,585 to Zipes, or U.S. Pat. No. 4,830,006 to Haluska et al., each of which patents are incorporated by reference herein in their entireties. The functional operation of the device illustrated in FIG. 1, other than as related to the present invention, is taken from allowed U.S. patent application Ser. No. 07/612,761, by Keimel et al, filed Nov. 14, 1991, also incorporated herein by reference in its entirety.

Control circuitry 44 provides several signals relevant to the operation of the present invention. First and second control signals, designated in FIG. 1 as NPULSE 1 and NPULSE 2, respectively, are signals for triggering the delivery of pacing, cardioverting, or defibrillating pulses. In particular, the NPULSE 1 signal triggers discharge of a first capacitor bank, comprising capacitors 56 and 58 in FIG. 1. The NPULSE 2 signal triggers discharge of the first capacitor bank and a second capacitor bank, comprising capacitors 60 and 62. Simply by modifying the number and time order of assertion of the NPULSE 1 and NPULSE 2 signals, it is possible to select between a plurality of output pulse regimes.

Another output signal from control circuitry 44 is designated HVCHG in FIG. 1. The HVCHG signal on line 45 goes high when it is necessary to charge output capacitors 56, 58, 60, and 62 prior to delivery of a therapeutic pulse by the device. Output capacitors 56, 58, 60, and 62 may be charged to very high voltages in the event that a defibrillation pulse is to be delivered. However, it is generally considered inefficient to maintain a constant charge on the output capacitors. Instead, it is more common that the capacitors would be quickly charged to a defibrillation or cardioversion voltage only upon detection of fibrillation or tachycardia.

Capacitors 56, 58, 60, and 62 are charged to a pre-programmed level by a high-voltage charging circuit 64, controlled by control circuitry 44 by means of bi-directional control/data bus 66. As illustrated, capacitors 56, 58, 60, and 62 are charged by means of a high-frequency, high-voltage transformer 68. Proper charging polarities are maintained by means of diodes 70, 72, and 74. VCAP line 54 provides a signal indicative of the voltage on the capacitor banks, and allows for control of the high voltage circuitry and for termination of the charging function when the stored voltage equals the programmed charging level. The details of the voltage charging circuitry are also not deemed to be critical with regard to practicing the present invention; one high voltage charging circuit believed to be suitable for the purposes of the present invention is disclosed in detail in the above-referenced U.S. Pat. No. 4,548,209 to Wielders et al.

In the Wielders patent, it is described how charging circuit 64 would be made responsive to an activation signal from control circuitry to charge the output capacitors. In the embodiment of the present invention depicted in FIG. 1 herein, the activation signal is a high HVCHG signal on line 45, which is coupled to high-voltage charging circuit 64.

As depicted in FIG. 1, the HVCHG signal on line 45 is additionally coupled to an external battery assembly 10 comprising a high energy density battery 12 and a switching circuit 14. The HVCHG signal on line 45 is applied to an input of switch 14, such that when HVCHG is high the positive terminal of battery 12 is coupled to EXT B+ line 18. When HVCHG is low, however, battery 12 is effectively isolated from EXT B+ line 18. EXT B− line 16 and EXT B+ line 18 are coupled to high-voltage charging circuit 64 to provide the energy necessary for charging output capacitors 56, 58, 60, and 62. Switch 14 may be, for example, a field effect transistor (FET) with its source-to-drain path disposed along the EXT B+ line and its gate receiving the HVCHG signal from line 45. Battery assembly 10 is contained in a separate hermetically-sealed housing, similar to a housing for an implantable pacemaker, with conductors exiting from the housing by means of feed-throughs, in a conventional manner.

In operation, the pacemaker/cardioverter/defibrillator of FIG. 1 monitors the patient's cardiac status and, in response to detection of an arrhythmic episode requiring delivery of a therapeutic pulse, initiates the charging of output capacitors 56, 58, 60, and 62 by a high HVCHG signal on line 45. When HVCHG is high this signal is applied via OR gate 51 and CHG line 49 to the control input of switch 14, thereby coupling the positive terminal of battery 12 to high-voltage charging circuit 64. Charging continues until the desired voltage is reflected on the VCAP line, at which point control circuit 44 sets the HVCHG signal on line 45 low, terminating charging and turning off switch 14. Typically, the charging cycle takes only fifteen to twenty seconds, and occurs very infrequently. Except during the relatively short charging cycle, there is no voltage differential between the EXT B+ and EXT B− lines 16 and 18, and thus the effect of leakage current in the connection between battery assembly 10 and the device is greatly reduced.

It may be desirable to include in high-voltage charging circuit 64 a simple delay circuit, as could be easily implemented by a person of ordinary skill in the circuit art. This delay circuit could cause a delay between assertion of the HVCHG line by control circuitry 44 and initiation of charging, leaving time for battery 12 to be coupled to the EXT B+ lines 18 before charging begins. Such a delay circuit is presently not considered to be essential for the practice of the present invention.

The separate hermetic enclosure containing the components of the pacemaker/cardioverter/defibrillator (those illustrated components not included in battery assembly 10) has a separate power supply therein in order to power the circuitry other than the high voltage charging circuitry. Since such power supply would not be utilized for the purposes of charging the device's output capacitor, it can be relatively small. Inclusion of separate power supplies in a implantable defibrillator has been common practice in the art, as recognized, for example, in the above-referenced Adams al. patent.

In the context of an implantable pacemaker/cardioverter/defibrillator, the internal battery may be a conventional lithium battery as presently used in cardiac pacemakers. However, the illustrated embodiment employs an internal battery 53, which may be a rechargeable battery, such as a nickel-cadmium battery, coupled to a low voltage charging circuit 55 appropriate for recharging the battery. Rechargeable battery systems for implantable devices are disclosed in U.S. Pat. No. 3,942,535, issued to Schulman, U.S. Pat. No. 4,197,850, issued to Schulman, et al and U.S. Pat. No. 4,232,679, issued to Schulman, all of which are incorporated herein by reference in their entireties. Alternatively, battery 51 may be replaced with a capacitor, and recharge circuitry 55 may simply take the form of a switch, coupling line 18 to the capacitor.

Regardless of the form of internal energy storage device, the voltage thereon is communicated to control logic 44 via line 57. In a manner analogous to that described above in conjunction with the operation of high voltage charging circuitry 64, control logic 44 generates a high logic signal on line 47, when necessary, which activates low voltage charging circuitry 55 and via OR gate 51, triggers switch 14 to connect the B+ line 18 to the positive terminal of the external battery 12. When internal battery 53 is fully charged, line 47 goes low, terminating charging and disconnecting line 18 from the positive terminal of the external battery 12. A similar rechargeable battery system may be employed to power cardiac pacemakers, nerve stimulators and the like.

Figure 2:
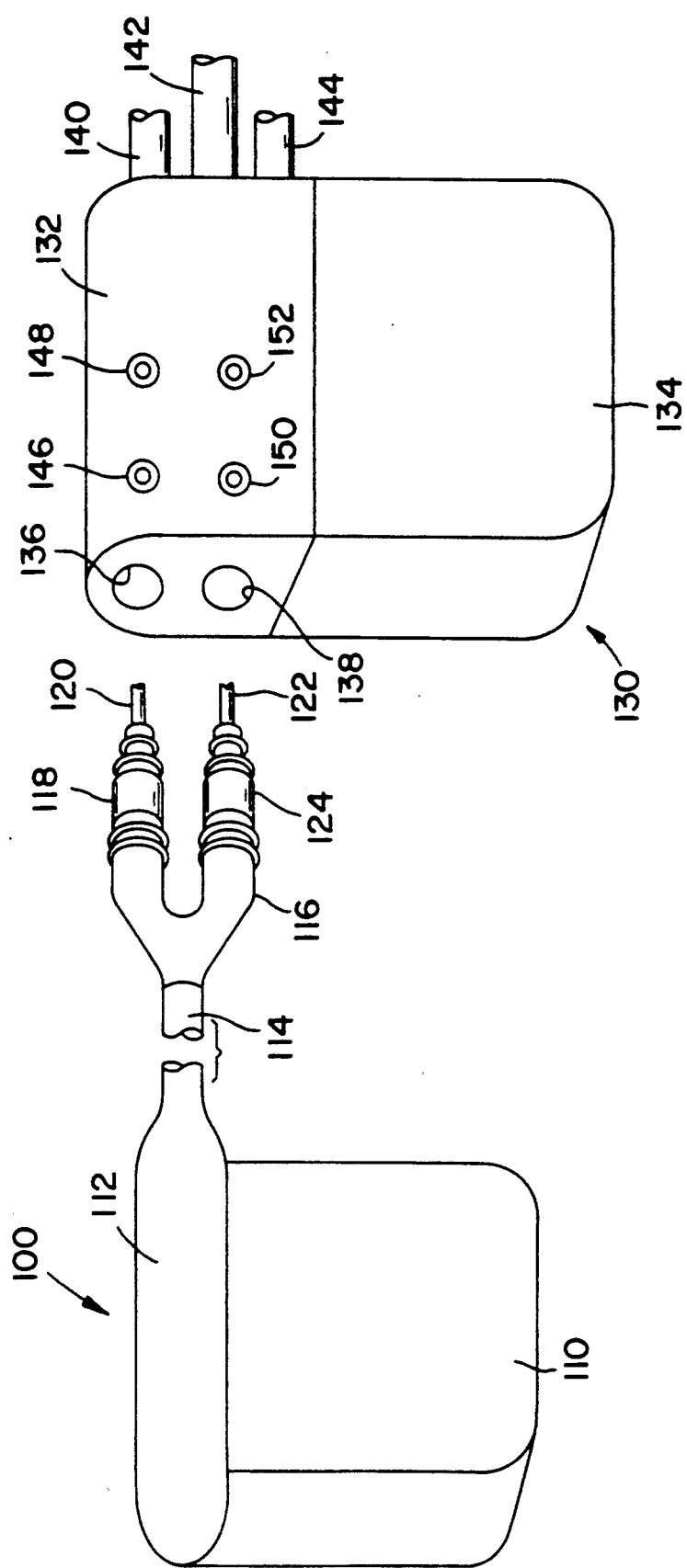
FIG. 2 is a perspective drawing of a first embodiment of the invention.
Figure 3:
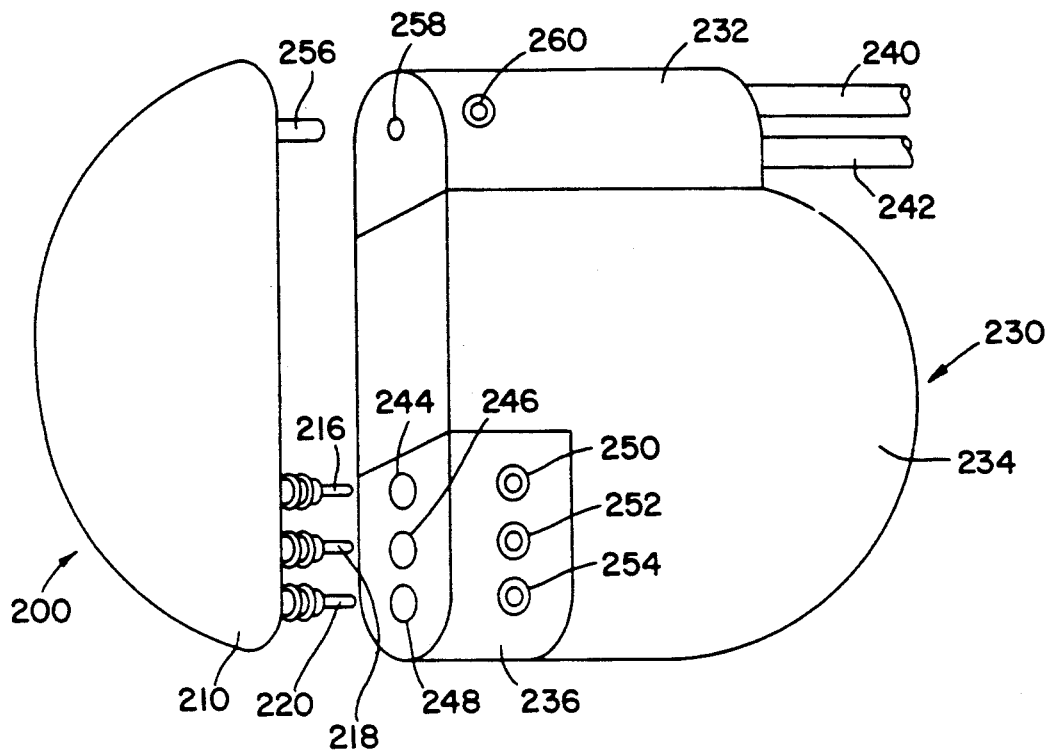
FIG. 3 is a perspective drawing of a second embodiment of the invention.
Figure 4:
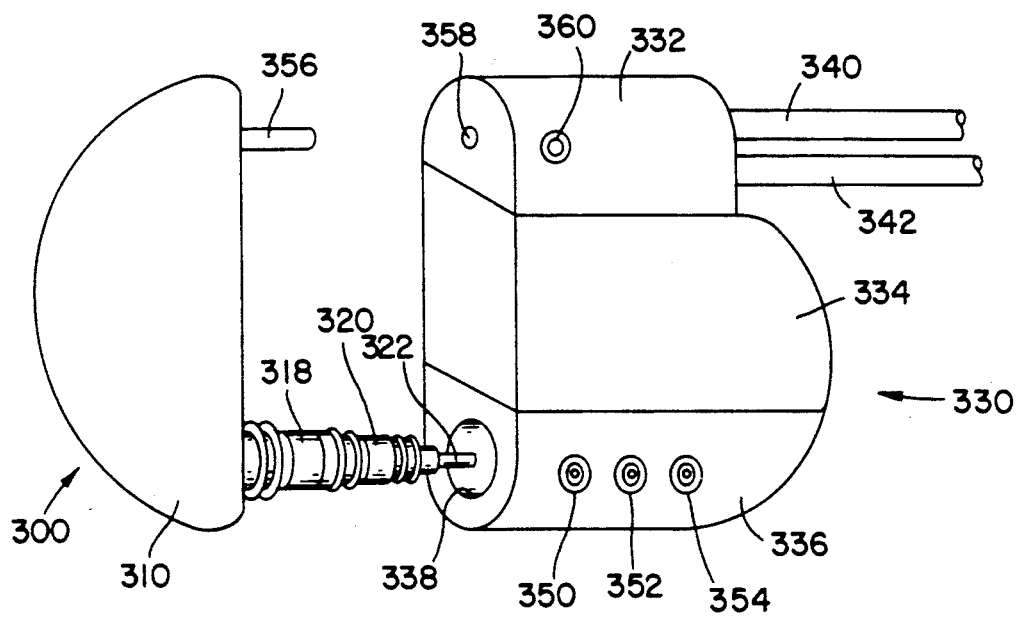
FIG. 4 is a perspective drawing of a third embodiment of the invention.

It is contemplated that any of the lead connector assemblies commonly known and/or commercially available would be suitable for the purposes of practicing the present invention, including those disclosed, for example, in U.S. Pat. No. 4,469,104 to Peers-Trevarton, U.S. Pat. No. 4,010,760 to Kraska et al., U.S. Pat. No. 4,445,511 to Cowdery et al., and U.S. Pat. No. 4,922,607 to Doan et al., each of which is hereby incorporated by reference in its entirety. FIGS. 2–4 illustrate alternative proposals for the mechanical configurations of devices according to the present invention, employing conventional pacing lead connector technology.

FIG. 2 illustrates a first proposed mechanical configuration for an apparatus generally as described in conjunction with FIG. 1. The device includes an external battery module 100 and an implantable pacemaker/cardioverter/defibrillator 130, with the components within external battery 100 corresponding to those illustrated within the confines of battery assembly 10, in FIG. 1. The battery and associated switch are located within a hermetically sealed housing 110, which may correspond to a standard pacemaker enclosure. Conductors coupled to the battery and switch therein extend outward through the upper surface of housing 110, through hermetic feedthroughs, in a conventional fashion, and are coupled to three elongated conductors which extend through an insulative lead body 114 to a connector assembly 116. As illustrated, the upper surface of the battery housing 110 is covered with a molded insulative boot 112, which may be molded of silicone rubber or other biocompatible insulative material.

Connector assembly 116 is bifurcated into two in-line connector assemblies of the type generally used in the cardiac pacing industry to couple bipolar pacing leads to implanted pulse generators. The connector assembly 116 includes connector pins 120 and 122, which may be coupled to the positive and negative terminals of the battery within housing 110, respectively and connector ring 118, which may be coupled to the control input of the switch within housing 110. Connector ring 124 relates to an optional feature, as will be discussed below.

The implantable pacemaker/cardioverter/defibrillator 130 includes the components not enclosed within the battery assembly 10 in FIG. 1, which are mounted within a second hermetically sealed housing 134, in a conventional fashion. Lines 16, 18 and 49 (FIG. 1) exit through the upper surface of the housing 134 through hermetic feedthroughs in a conventional fashion and are mounted to connector blocks associated with bores 136 and 138 in molded connector assembly 132. Connector bores 136 and 138 and the connector blocks associated with them may correspond to those used on implantable pacemakers, for use in conjunction with electrical lead connectors meeting the IS-1 international standard. Grommets 146, 148 and 152 allow access to internal set screws within the connector blocks may which are advanced into contact with connector ring 118 and connector pins 120 and 122, in a conventional fashion. Grommet 150 correspondingly provides access to a connector block in bore 138, for connecting to ring 124. Also illustrated are the proximal ends of leads 140, 142 and 144 also exiting from connector assembly 132. Leads 140, 142 and 144 include pacing, sensing and defibrillation electrodes of the typically used in conjunction with implantable pacemaker/cardioverter/defibrillators presently in clinical evaluation in the United States, and are inserted in corresponding connector bores within connector assembly 132.

In the embodiment of FIG. 2, the external battery and the implantable device need not be located adjacent to one another, providing added flexibility in locating the pacemaker/cardioverter/defibrillator. This may be especially desirable in the event that the housing 134 of the defibrillator is intended for use as an electrode, in a location which would not permit implant of a corresponding device with an internal battery. In addition, as an alternative embodiment, connector ring 124 could be coupled to an additional conductor located within lead assembly 114, and thereby coupled to the housing 110 of the battery assembly 100. A connector block in bore 138 which couples to ring 124 could be connected to a high voltage output of the device, which in turn would allow housing 110 to be used as an additional subcutaneous cardioversion or defibrillation electrode.

FIG. 3 illustrates an alternative embodiment in which the battery and the device (in this case, a pacemaker) are adapted to be combined in a fashion that simulates the overall external configuration of prior art implantable cardiac pacemakers. In this embodiment, the device circuitry is located within hermetically sealed housing 234, and includes circuitry corresponding to that illustrated in FIG. 1, with the deletion of circuit blocks and components associated with generation of high voltage output pulses. The housing 234 is provided with two connector assemblies 232 and 236. Connector assembly 232 comprises a standard connector assembly for coupling the device to cardiac pacing and sensing leads 240 and 242. Connector assembly 236 serves to couple the external battery assembly 200 to the pacemaker 230.

The battery assembly 200 includes a battery and a switch corresponding to those illustrated in Box 10 of FIG. 1, mounted within a hermetic enclosure 210. The positive and negative terminals of the battery within housing 210 and the switch control line are coupled to connector pins 216, 218 and 220, which take a form corresponding to the connector assemblies used in conjunction with unipolar pacing leads for many years. Connector block 236 is provided with three bores, 244, 246 and 248, each of which includes a conventional connector block of the type used to connect unipolar pacing leads to cardiac pacemakers. Access to set screws within the connector blocks is accomplished via grommets 150, 152 and 154, in a conventional fashion. In order to provide a firmer mechanical interconnection between the devices, a pin 156 is provided mounted to the exterior of housing 110. Connector block 232 on the pacemaker 230 is provided with a bore 258 for receiving pin 256 and a corresponding connector block therein for attaching connector block 232 to pin 156. Access to the connector block within connector assembly 232 is obtained via grommet 260, in a conventional fashion.

In conjunction with FIG. 3 it should also be noted that in the event the circuitry within the device so permits, the negative terminal battery within housing 210 may be coupled to the housing itself. In this case, one of the three connector pins 216, 218 and 220 may be deleted, and connection to the housing 210 and thereby to the negative terminal of the battery therein may be accomplished using pin 156, and by coupling the connector block within bore 158 either to circuitry internal to the pacemaker or to the housing 234 of the device, if the negative terminal of the internal battery is correspondingly coupled to housing 234.

FIG. 4 illustrates yet another alternative embodiment, corresponding generally to that illustrated in FIG. 3. Like the device in FIG. 3, the pacemaker or other stimulator 330 is provided with two connector assemblies 332 and 336. Connector assembly 332 and associated grommet 360, bore 358 and leads 340 and 342 correspond to connector assembly 232, sealing grommet 260, bore 258 and leads 240 and 242 illustrated in FIG. 3. Similarly, external battery 300, housing 310 and pin 356 correspond to external battery 200, housing 210 and pin 256 illustrated in FIG. 3.

The device of FIG. 4 substitutes a tripolar in-line connector assembly for the three separate electrical connectors 216, 218 and 220 illustrated in FIG. 3. In-line connector assembly may correspond to that illustrated in the above-cited Doan et al. patent application, and carries two connector rings 318, 320 and a connector pin 322. Connector assembly 336 is correspondingly provided with a stepped bore 338 in which connector assembly 316 is inserted. Connector bore 334 is provided with three internal connector blocks linearly arranged along the length of the bore, for engaging with connector rings 318, 320 and connector pin 322. Access to the set screws associated with the connector blocks arranged along bore 334 is obtained via grommets 350, 352 and 354, in a conventional fashion. As discussed above in conjunction with the embodiment illustrated in FIG. 3, in the event that the circuitry permits connection of the negative terminal of the battery to the housing 310, pin 356 may be used to connect the negative terminal of the battery either to the housing 334 of the device or the circuitry therein. In this case, connector assembly 316 would be replaced by a bipolar in-line connector, of the sort typically used in conjunction with bipolar cardiac pacing leads, and connector assembly 336 would be replaced by a single bipolar connector assembly of the sort typically used to couple cardiac pacemakers to pacing leads meeting the IS-1 standard.

From the foregoing detailed description of specific embodiments of the invention, it should be apparent that a method and apparatus for providing a detachable, replaceable battery for an implantable device has been disclosed which overcomes the problem of current leakage associated with non-hermetic coupling of batteries to implanted devices. Although particular embodiments of the invention have been disclosed herein in some detail, this has been done for the purposes of illustration only. It is contemplated that various substitutions, alterations, and modifications may be made to the disclosed embodiment of the invention without departing from the spirit and scope of the invention as defined in the appended claims.

What is claimed is:

1. An implantable medical device, comprising:
   a first hermetically sealed enclosure containing a capacitor and electrical circuitry including control means for generating a control signal and provided with a first connector means for coupling to said capacitor and a second connector means for coupling to said control means, said enclosure further comprising output connector means for coupling to body stimulation electrodes, and means for connecting said capacitor to said output connector means for discharging said capacitor to stimulate body tissue; and
   a second hermetically sealed enclosure, containing a battery and a switch having a control input, and provided with third connector means for removably coupling to said first connector means, and fourth connector means for removably coupling to said second connector means, said fourth connector means coupled to said control input of said switch, said switch comprising means for coupling said battery to said third connector means responsive to a control signal applied at said control input.

2. An implantable medical device, according to claim 1 wherein said electrical circuitry comprises charging circuitry for charging said capacitor to a desired voltage.

3. An implantable cardioverter or defibrillator, comprising:
   a first hermetically sealed enclosure containing an output capacitor, a charging circuit for charging said output capacitor to a desired voltage and electrical circuitry including control means for generating a control signal and provided with a first connector means for coupling to said charging circuit and a second connector for coupling to said control means, said first enclosure further provided with output connector means for coupling to body stimulation electrodes and wherein said electrical circuitry comprises circuitry coupled to said output connector means for discharging said capacitor to stimulate body tissue; and a second hermetically sealed enclosure, containing a battery and a switch having a control input, and provided with third connector means for removably coupling to said first connector means, and fourth connector means for removably coupling said to second connector means, said fourth connector means coupled to said control input of said switch, said switch comprising means for coupling said battery to said third connector means responsive to a control signal applied at said control input.

4. An implantable cardioverter or defibrillator according to claim 3 wherein said first hermetically sealed enclosure further comprises an internal energy storage means for powering said electrical circuitry, including said control means.

5. An implantable cardioverter or defibrillator according to claim 4 wherein said first hermetically sealed enclosure comprises a cardiac pacemaker and wherein said internal energy storage means comprises means for powering said cardiac pacemaker.

* * * * *